US012558183B2

(12) United States Patent
Misener et al.

(10) Patent No.: US 12,558,183 B2
(45) Date of Patent: Feb. 24, 2026

(54) FENESTRATION COVERINGS, PROCEDURAL DRAPES, AND METHODS THEREOF

(71) Applicant: Bard Access Systems, Inc., Salt Lake City, UT (US)

(72) Inventors: Anthony K. Misener, Bountiful, UT (US); Steffan Sowards, Salt Lake City, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 1094 days.

(21) Appl. No.: 17/487,407

(22) Filed: Sep. 28, 2021

(65) Prior Publication Data

US 2022/0096190 A1 Mar. 31, 2022

Related U.S. Application Data

(60) Provisional application No. 63/085,059, filed on Sep. 29, 2020.

(51) Int. Cl.
*A61B 46/00* (2016.01)
*A61B 46/20* (2016.01)

(52) U.S. Cl.
CPC .............. *A61B 46/40* (2016.02); *A61B 46/20* (2016.02); *A61B 2046/205* (2016.02)

(58) Field of Classification Search
CPC ......... A61B 46/10; A61B 46/17; A61B 46/23; A61B 46/40; A61B 2046/205; A61B 2046/234

See application file for complete search history.

(56) References Cited

U.S. PATENT DOCUMENTS

| | | | |
|---|---|---|---|
| 3,799,161 A | 3/1974 | Collins | |
| 4,627,427 A * | 12/1986 | Arco | A61B 46/00 128/853 |
| 2011/0301459 A1 | 12/2011 | Gharib | |
| 2014/0026895 A1 | 1/2014 | Hodges et al. | |
| 2016/0081751 A1* | 3/2016 | Marshburn | A61B 46/30 128/854 |
| 2021/0045829 A1* | 2/2021 | Bishop | A61B 6/4441 |
| 2021/0307856 A1* | 10/2021 | Aguirre | A61B 46/40 |

OTHER PUBLICATIONS

PCT/US2021/052347 filed Sep. 28, 2021 International Search Report and Written Opinion dated Jan. 21, 2022.

* cited by examiner

*Primary Examiner* — Camtu T Nguyen
(74) *Attorney, Agent, or Firm* — Rutan & Tucker LLP

(57) ABSTRACT

Disclosed are fenestration coverings, procedural drapes, and methods thereof. For example, a fenestration covering is configured to cover a fenestration in a procedural drape for a medical procedure. The fenestration covering includes a transparent sheet of polymeric material and a non-adhesive central portion of the fenestration covering. The transparent sheet has a length and width sufficient to cover the fenestration and allow a clinician to manipulate the patient, one or more pieces of procedural equipment or supplies, or a combination thereof under the fenestration covering. The central portion of the fenestration covering is greater than or coextensive with the fenestration. An example method includes forming a fenestration in one or more procedural drapes for a medical procedure and covering the fenestration with the fenestration covering.

23 Claims, 4 Drawing Sheets

108

106

106

104

100

102

108

100

102

FENESTRATION COVERINGS, PROCEDURAL DRAPES, AND METHODS THEREOF

PRIORITY

This application claims the benefit of priority to U.S. Provisional Application No. 63/085,059, filed Sep. 29, 2020, which is incorporated by reference in its entirety into this application.

BACKGROUND

A procedural field is typically established around a patient with one or more procedural drapes before a medical procedure. For example, a sterile field can be established around a patient by covering the patient with a sterile but opaque procedural drape. Typically, only small fenestrations are available in sterile drapes for visual and palpable access of disinfected portions of patients. As a consequence, clinicians are largely blind to non-disinfected portions of the patients lying under the sterile drapes outside of the small fenestrations. What is needed is a way for clinicians to view and palpate patients under procedural drapes, as well as manipulate any medical devices under the procedural drapes.

Disclosed herein are fenestration coverings, procedural drapes, and methods thereof that address the foregoing.

SUMMARY

A fenestration covering for a fenestration in a procedural drape for a medical procedure is disclosed. The fenestration covering includes a transparent sheet of polymeric material and a non-adhesive central portion of the fenestration covering. The transparent sheet has a length and width sufficient to cover the fenestration and allow a clinician to manipulate the patient, one or more pieces of procedural equipment or supplies, or a combination thereof under the fenestration covering. The central portion of the fenestration covering is greater than or coextensive with the fenestration.

In some embodiments, the fenestration covering further includes margins around the central portion of the fenestration covering. The margins include a pair of opposing longitudinal margins and a pair of transverse margins in which at least one pair of margins of the pairs of longitudinal and transverse margins includes a reusable adhesive configured for adhering the fenestration covering to the procedural drape.

In some embodiments, the fenestration covering further includes margins around the central portion of the fenestration covering. The margins include a pair of opposing longitudinal margins and a pair of transverse margins in which at least one pair of margins of the pairs of longitudinal and transverse margins includes a single-use adhesive configured for adhering the fenestration covering to the procedural drape.

In some embodiments, the polymeric material is a breathable polyethylene, polypropylene, or polyurethane.

In some embodiments, the polymeric material is impregnated with a broad-spectrum antimicrobial.

In some embodiments, the central portion of the fenestration covering is breachable by a piece of procedural equipment of the one-or-more pieces of procedural equipment.

In some embodiments, the fenestration covering is a sterile fenestration covering.

A procedural drape for a medical procedure is also disclosed. The procedural drape includes a transparent sheet of polymeric material and a non-adhesive central portion of the procedural drape. The transparent sheet has a length and width sufficient to establish a procedural field about a patient for the medical procedure. The central portion of the procedural drape is configured to cover the patient without adhering to the patient, thereby allowing a clinician to manipulate the patient, one or more pieces of procedural equipment or supplies, or a combination thereof under the procedural drape.

In some embodiments, the procedural drape further includes margins around the central portion of the procedural drape. The margins include a pair of opposing longitudinal margins and a pair of transverse margins in which at least one pair of margins of the pairs of longitudinal and transverse margins includes a reusable adhesive configured for adhering the procedural drape to one or more other procedural drapes or surfaces.

In some embodiments, the procedural drape further includes margins around the central portion of the procedural drape. The margins include a pair of opposing longitudinal margins and a pair of transverse margins in which at least one pair of margins of the pairs of longitudinal and transverse margins includes a single-use adhesive configured for adhering the procedural drape to one or more other procedural drapes or surfaces.

In some embodiments, the polymeric material is a breathable polyethylene, polypropylene, or polyurethane.

In some embodiments, the polymeric material is impregnated with a broad-spectrum antimicrobial.

In some embodiments, the central portion of the procedural drape is breachable by a piece of procedural equipment of the one-or-more pieces of procedural equipment.

In some embodiments, the procedural drape is a sterile procedural drape.

Another procedural drape for a medical procedure is disclosed. The procedural drape includes an opaque sheet of one or more nonwoven materials, a transparent sheet of polymeric material on a side of the opaque sheet, and one or more fenestrations in the opaque sheet. The opaque sheet has a length and width sufficient to establish a procedural field about a patient for the medical procedure. The transparent sheet is coextensive with the length and the width of the opaque sheet. The transparent sheet provides one or more fenestration coverings covering the one-or-more fenestrations, thereby allowing a clinician to manipulate the patient, one or more pieces of procedural equipment or supplies, or a combination thereof under the one-or-more fenestration coverings.

In some embodiments, the procedural drape further includes margins around a central portion of the procedural drape. The margins include a pair of opposing longitudinal margins and a pair of transverse margins in which at least one pair of margins of the pairs of longitudinal and transverse margins includes a reusable adhesive configured for adhering the procedural drape to one or more other procedural drapes or surfaces.

In some embodiments, the procedural drape further includes margins around a central portion of the procedural drape. The margins include a pair of opposing longitudinal margins and a pair of transverse margins in which at least one pair of margins of the pairs of longitudinal and transverse margins includes a single-use adhesive configured for adhering the procedural drape to one or more other procedural drapes or surfaces.

In some embodiments, the opaque sheet includes one or more plies. Each ply of the one-or-more plies is of a nonwoven material selected from a polypropylene or a wood pulp.

In some embodiments, the opaque sheet includes a single ply of spunbond polypropylene.

In some embodiments, the opaque sheet includes a single ply of spunlace wood pulp.

In some embodiments, the opaque sheet includes one ply of meltblown polypropylene between two plies of spunbond polypropylene.

In some embodiments, the polymeric material is a breathable polyethylene, polypropylene, or polyurethane.

In some embodiments, the polymeric material is impregnated with a broad-spectrum antimicrobial.

In some embodiments, the one-or-more fenestration coverings are breachable by a piece of procedural equipment of the one-or-more pieces of procedural equipment.

In some embodiments, the procedural drape is a sterile procedural drape.

Yet another procedural drape for a medical procedure is disclosed. The procedural drape includes an opaque sheet of one or more nonwoven materials, a transparent sheet of polymeric material on a side of the opaque sheet, and one or more removable pieces of the opaque sheet. The opaque sheet has a length and width sufficient to establish a procedural field about a patient for the medical procedure. The transparent sheet is coextensive with the length and the width of the opaque sheet. The one-or-more removable pieces of the opaque sheet are configured for respectively forming one or more fenestrations in the opaque sheet upon removal of the one-or-more removable pieces. The transparent sheet provides one or more fenestration coverings covering the one-or-more fenestrations, thereby allowing a clinician to manipulate the patient, one or more pieces of procedural equipment or supplies, or a combination thereof under the one-or-more fenestration coverings.

In some embodiments, the one-or-more removable pieces have perforated or precut perimeters configured to facilitate removal of the one-or-more removable pieces.

In some embodiments, the one-or-more removable pieces include a reusable adhesive configured for adhering the one-or-more removable pieces to the transparent sheet.

In some embodiments, the procedural drape further includes margins around a central portion of the procedural drape. The margins include a pair of opposing longitudinal margins and a pair of transverse margins in which at least one pair of margins of the pairs of longitudinal and transverse margins includes a same or different reusable adhesive configured for adhering the procedural drape to one or more other procedural drapes or surfaces.

In some embodiments, the procedural drape further includes margins around a central portion of the procedural drape. The margins include a pair of opposing longitudinal margins and a pair of transverse margins in which at least one pair of margins of the pairs of longitudinal and transverse margins includes a single-use adhesive configured for adhering the procedural drape to one or more other procedural drapes or surfaces.

In some embodiments, the opaque sheet includes one or more plies. Each ply of the one-or-more plies is of a nonwoven material selected from a polypropylene or a wood pulp.

In some embodiments, the opaque sheet includes a single ply of spunbond polypropylene.

In some embodiments, the opaque sheet includes a single ply of spunlace wood pulp.

In some embodiments, the opaque sheet includes one ply of meltblown polypropylene between two plies of spunbond polypropylene.

In some embodiments, the polymeric material is a breathable polyethylene, polypropylene, or polyurethane.

In some embodiments, the polymeric material is impregnated with a broad-spectrum antimicrobial.

In some embodiments, the one-or-more fenestration coverings are breachable by a piece of procedural equipment of the one-or-more pieces of procedural equipment.

In some embodiments, the procedural drape is a sterile procedural drape.

A method for a fenestration covering is also disclosed. The method includes a forming step, a covering step, and a manipulating step. The forming step includes forming a fenestration in one or more procedural drapes for a medical procedure. The covering step includes covering the fenestration with the fenestration covering. The fenestration covering includes a transparent sheet of polymeric material having a length and width sufficient to cover the fenestration. The fenestration covering also includes a non-adhesive central portion of the fenestration covering greater than or coextensive with the fenestration. The manipulating step includes manipulating the patient, one or more pieces of procedural equipment or supplies, or a combination thereof under the fenestration covering.

In some embodiments, the forming step includes cutting out at least one piece of at least one procedural drape of the one-or-more procedural drapes to form the fenestration.

In some embodiments, the forming step includes arranging several procedural drapes of the one-or-more procedural drapes to form the fenestration.

In some embodiments, the method further includes an adhering step. The adhering step includes adhering the fenestration covering to the one-or-more procedural drapes. The fenestration covering includes margins around the central portion of the fenestration covering including a pair of opposing longitudinal margins and a pair of transverse margins in which at least one pair of margins of the pairs of longitudinal and transverse margins includes a reusable adhesive configured for the adhering step.

In some embodiments, the method further includes an adhering step. The adhering step includes adhering the fenestration covering to the one-or-more procedural drapes. The fenestration covering includes margins around the central portion of the fenestration covering including a pair of opposing longitudinal margins and a pair of transverse margins in which at least one pair of margins of the pairs of longitudinal and transverse margins includes a single-use adhesive configured for the adhering step.

These and other features of the concepts provided herein will become more apparent to those of skill in the art in view of the accompanying drawings and following description, which describe particular embodiments of such concepts in greater detail.

DRAWINGS

DESCRIPTION

Figures 1, 2:
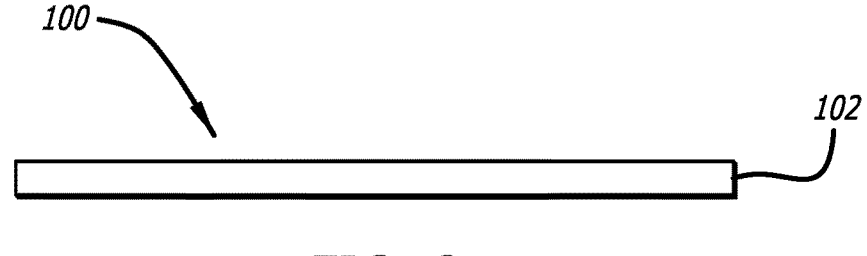
FIG. 1 illustrates a top view of a transparent fenestration covering or procedural drape in accordance with some embodiments.
FIG. 2 illustrates a side view of the fenestration covering or procedural drape of FIG. 1 in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, clinicians have a need to view and palpate patients under procedural drapes, as well as manipulate any medical devices under the procedural drapes. Disclosed herein are fenestration coverings, procedural drapes, and methods thereof that address the foregoing.

Fenestration Coverings

FIG. 1 illustrates a top view of a transparent fenestration covering 100 in accordance with some embodiments. FIG. 2 illustrates a side view of the fenestration covering 100 of FIG. 1 in accordance with some embodiments.

The fenestration covering 100 is configured to cover one or more fenestrations in a procedural drape for a medical procedure. For example, the fenestration covering 100 can be a sterile fenestration covering configured to cover one or more fenestrations in a sterile drape.

The fenestration covering 100 includes a transparent sheet 102 of polymeric material such as a single non-laminated transparent sheet of polymeric material or two-or-more layers of polymeric material laminated together in a laminated transparent sheet. Regardless, the transparent sheet 102 has a length and width sufficient to cover the one-or-more fenestrations in the procedural drape, as well as a flexibility to allow a clinician to manipulate a patient, one or more pieces of procedural equipment or supplies, or a combination thereof under the fenestration covering.

The polymeric material of the transparent sheet 102 can be a porous, breathable polymeric film such as a polyethylene, a polypropylene, or a polyurethane. For the laminated transparent sheet, each layer of the two-or-more layers can include a same or different polymeric material than an adjacent layer of the two-or-more layers of the laminated transparent sheet. The polymeric material in the non-laminated transparent sheet or in any layer of the two-or-more layers of the laminated transparent sheet can also be impregnated with a broad-spectrum antimicrobial (e.g., an iodophor) to impart antimicrobial activity to the fenestration covering.

The fenestration covering 100 also includes at least a non-adhesive central portion 104. The non-adhesive central portion 104 of the fenestration covering 100 can be defined by margins around the central portion of the fenestration covering such as a pair of opposing longitudinal margins 106 and a pair of opposing transverse margins 108. One pair or both pairs of margins of the pairs of longitudinal and transverse margins 106 and 108 can include a single-use or reusable adhesive configured for adhering the fenestration covering 100 to the procedural drape.

Being that the central portion 104 of the fenestration covering 100 coincides with a central portion of the transparent sheet 102, the central portion 104 of the fenestration covering 100 is breachable by a piece of procedural equipment of the one-or-more pieces of procedural equipment. Indeed, the central portion 104 of the fenestration covering 100 being breachable is useful for connecting sterile consumable equipment in a sterile field above a combination of a sterile fenestration covering and a sterile drape to non-sterile reusable equipment below the combination.

Procedural Drapes

FIG. 1 alternatively illustrates a top view of a procedural drape 100 in accordance with some embodiments. FIG. 2 illustrates a side view of the procedural drape 100 of FIG. 1 in accordance with some embodiments.

The procedural drape 100 is configured to cover a patient or one or more portions of the patient for a medical procedure. For example, the procedural drape 100 can be a sterile drape configured to cover the patient or the one-or-more portions of the patient.

The procedural drape 100 includes a transparent sheet 102 of polymeric material such as a single non-laminated transparent sheet of polymeric material or two-or-more layers of polymeric material laminated together in a laminated transparent sheet. Regardless, the transparent sheet 102 has a length and width sufficient to establish a procedural field about a patient for the medical procedure, as well as a flexibility to allow a clinician to manipulate the patient, one or more pieces of procedural equipment or supplies, or a combination thereof under the procedural drape 100.

The polymeric material of the transparent sheet 102 can be a porous, breathable polymeric film such as a polyethylene, a polypropylene, or a polyurethane. For the laminated transparent sheet, each layer of the two-or-more layers can include a same or different polymeric material than an adjacent layer of the two-or-more layers of the laminated transparent sheet. The polymeric material in the non-laminated transparent sheet or in any layer of the two-or-more layers of the laminated transparent sheet can be also be impregnated with a broad-spectrum antimicrobial (e.g., an iodophor) to impart antimicrobial activity to the procedural drape 100.

The procedural drape 100 also includes at least a non-adhesive central portion 104 configured to cover the patient without adhering to the patient, thereby allowing a clinician to manipulate the patient, the one-or-more pieces of procedural equipment or supplies, or a combination thereof under the procedural drape 100. The non-adhesive central portion 104 of the procedural drape 100 can be defined by margins around the central portion 104 of the procedural drape 100 such as a pair of opposing longitudinal margins 106 and a pair of opposing transverse margins 108. One pair or both pairs of margins of the pairs of longitudinal and transverse margins 106 and 108 can include a single-use or reusable adhesive configured for adhering the procedural drape 100 to one or more other procedural drapes or surfaces.

Being that the central portion 104 of the procedural drape 100 coincides with a central portion of the transparent sheet, the central portion 104 of the procedural drape 100 is breachable by a piece of procedural equipment of the one-or-more pieces of procedural equipment. Indeed, the central portion 104 of the procedural drape 100 being breachable is useful for connecting sterile consumable equipment in a sterile field above a sterile procedural drape to non-sterile reusable equipment below the procedural drape 100.

Figures 3, 4, 5:
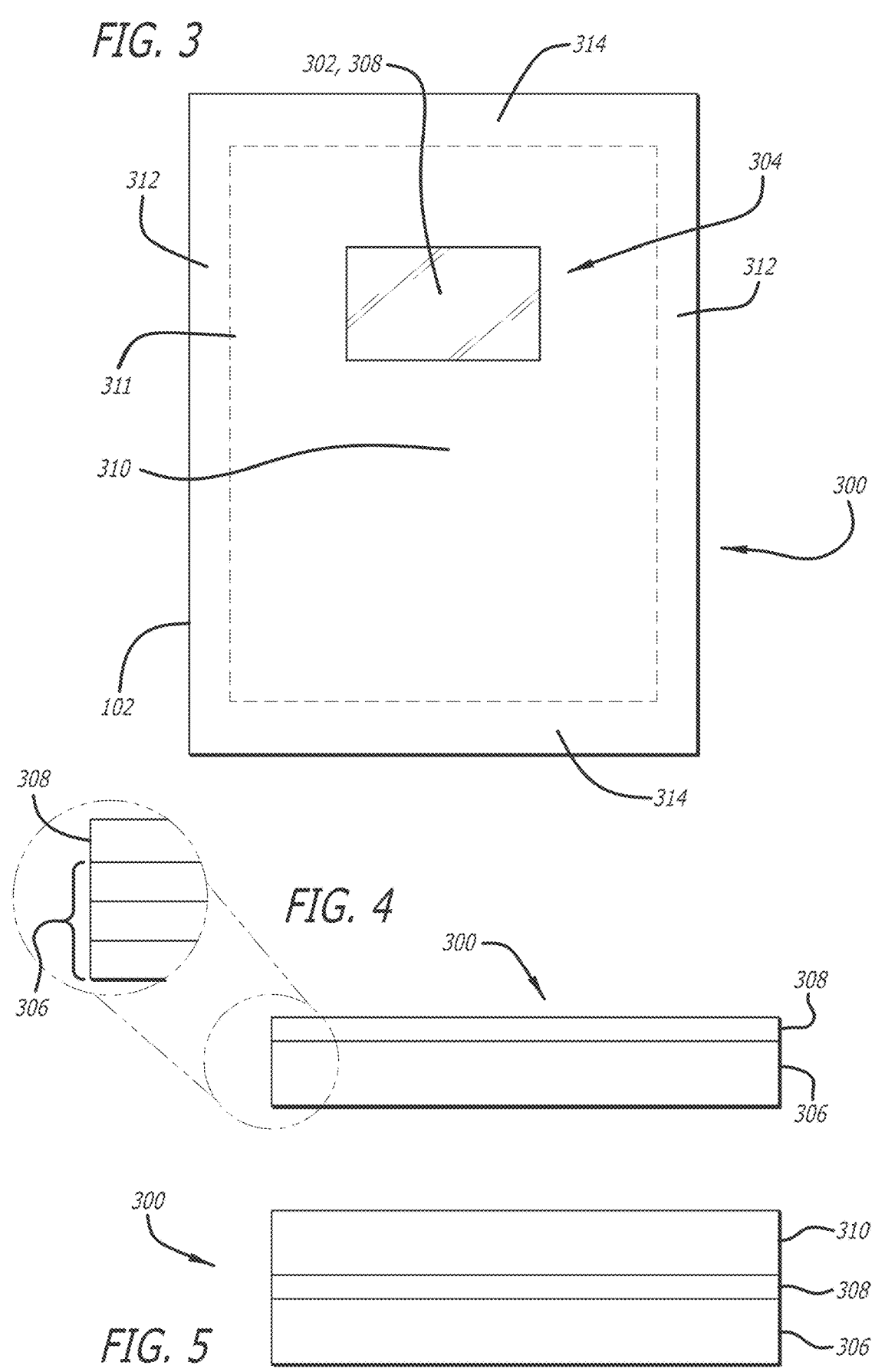
FIG. 3 illustrates a top view of a procedural drape with one or more fenestration coverings respectively covering one or more fenestrations in accordance with some embodiments.
FIG. 4 illustrates a side view of the procedural drape of FIG. 3 in accordance with some embodiments.
FIG. 5 illustrates a side view of the procedural drape of FIG. 3 in accordance with some other embodiments.

FIG. 3 illustrates a top view of a procedural drape 300 with one or more fenestration coverings 302 respectively covering one or more fenestrations 304 in accordance with some embodiments. FIGS. 4 and 5 illustrate side views of the procedural drape 300 of FIG. 3 in accordance with some embodiments.

The procedural drape 300 is configured to cover a patient or one or more portions of the patient for a medical procedure. For example, the procedural drape 300 can be a sterile drape configured to cover the patient or the one-or-more portions of the patient.

The procedural drape 300 includes an opaque sheet 306 of one or more nonwoven materials, a transparent sheet 308 of polymeric material on a side of the opaque sheet 306 forming a laminate thereof (see FIG. 4), and the one-or-more fenestrations 304 in the opaque sheet 306. A same or different opaque sheet 310 of the one-or-more nonwoven materials including the same one-or-more fenestrations 304 is optionally on a side of the transparent sheet 308 forming another laminate (see FIG. 5). The procedural drape 300 including at least the opaque sheet 306 and the transparent sheet 308 has a length and width sufficient to establish a procedural field about the patient with the transparent sheet 308 providing the one-or-more fenestration coverings 302 respectively covering the one-or-more fenestrations 304, thereby allowing a clinician to manipulate the patient, one or more pieces of procedural equipment or supplies, or a combination thereof under the one-or-more fenestration coverings 302 having a flexibility therefor.

The opaque sheet 306 includes a single ply of the one-or-more nonwoven materials or two or more plies of the one-or-more nonwoven materials. The nonwoven material of any ply of the opaque sheet 306 can be a polypropylene or a wood pulp. In other words, the single ply or each ply of the two-or-more plies of the opaque sheet 306 can independently be a polypropylene or a wood pulp. For example, the opaque sheet 306 can be a single ply of spunbond polypropylene. Alternatively, the opaque sheet 306 can be a single ply of spunlace wood pulp. Such embodiments are exemplified in the main portions of FIGS. 4 and 5. In another example, the opaque sheet 306 includes one ply of melt-blown polypropylene between two plies of spunbond polypropylene. Such an embodiment is exemplified in the inset portion of FIG. 4.

The transparent sheet 308 includes a single non-laminated transparent sheet of polymeric material or two-or-more layers of polymeric material laminated together in a laminated transparent sheet. Regardless, the transparent sheet 308 is coextensive with the length and the width of the opaque sheet 306. Like that set forth above, the polymeric material of the transparent sheet 308 can be a porous, breathable polymeric film such as a polyethylene, a polypropylene, or a polyurethane. For the laminated transparent sheet, each layer of the two-or-more layers can include a same or different polymeric material than an adjacent layer of the two-or-more layers of the laminated transparent sheet. The polymeric material in the non-laminated transparent sheet or in any layer of the two-or-more layers of the laminated transparent sheet can also be impregnated with a broad-spectrum antimicrobial (e.g., an iodophor) to impart antimicrobial activity to the fenestration covering 302.

The procedural drape 300 also includes margins around a central portion 311 of the procedural drape 300 such as a pair of opposing longitudinal margins 312 and a pair of opposing transverse margins 314. One pair or both pairs of margins of the pairs of longitudinal and transverse margins 312 and 314 can include a single-use or reusable adhesive configured for adhering the procedural drape 300 to one or more other procedural drapes or surfaces.

The one-or-more fenestrations 304 in the opaque sheet 306 can be of any shape or size. Being that the one-or-more fenestration coverings 302 respectively covering the one-or-more fenestrations 304 are provided by the transparent sheet 308, the one-or-more fenestration coverings 302 are breachable by a piece of procedural equipment of the one-or-more pieces of procedural equipment. Like that set forth above, this is useful for connecting sterile consumable equipment in a sterile field above a sterile procedural drape to non-sterile reusable equipment below the procedural drape 300.

Figures 6, 7, 8:
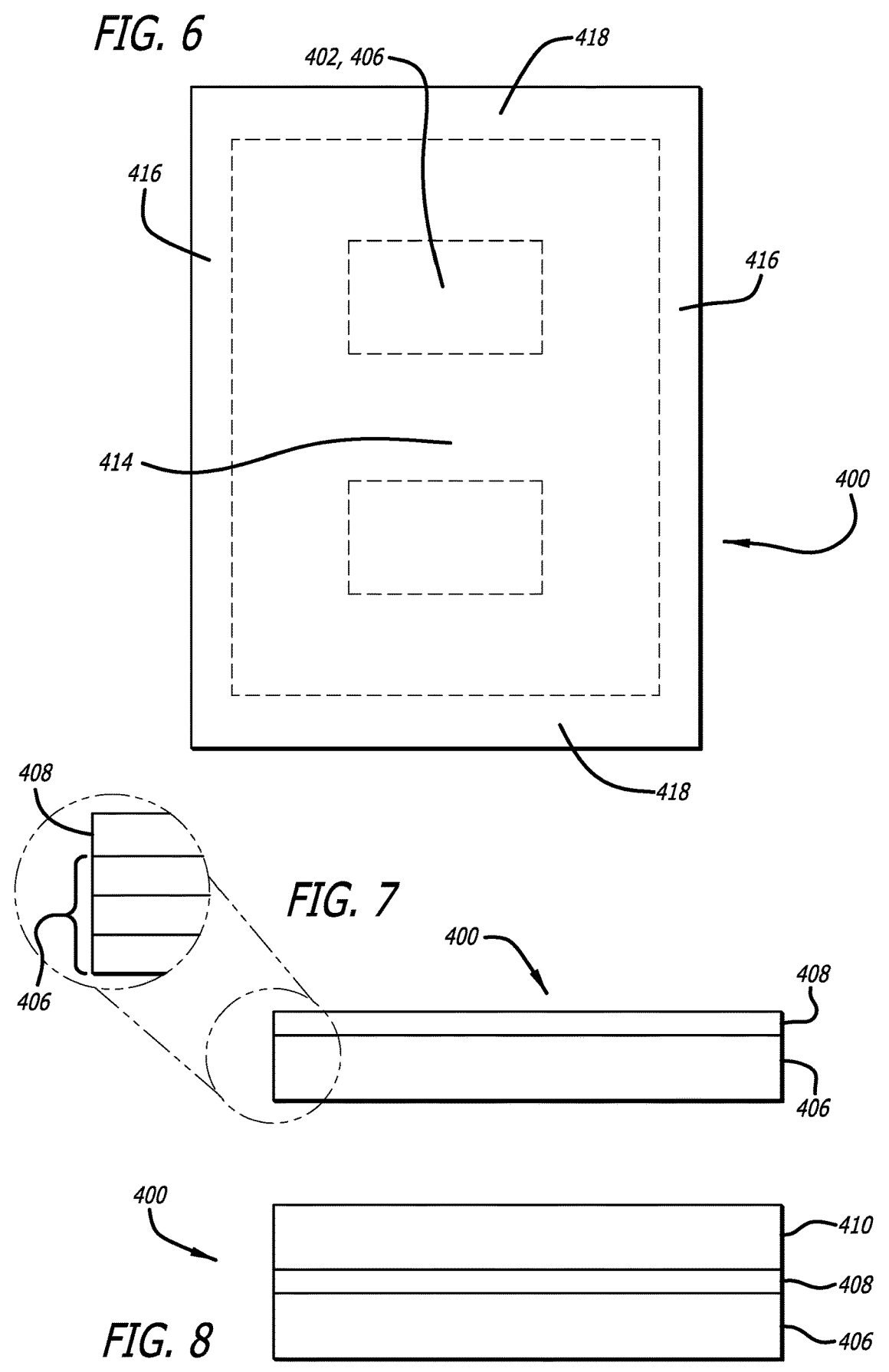
FIG. 6 illustrates a top view of a procedural drape with one or more removable pieces for respectively forming one or more covered fenestrations in accordance with some embodiments.
FIG. 7 illustrates a side view of the procedural drape of FIG. 6 in accordance with some embodiments.
FIG. 8 illustrates a side view of the procedural drape of FIG. 6 in accordance with some other embodiments.
Figure 9:
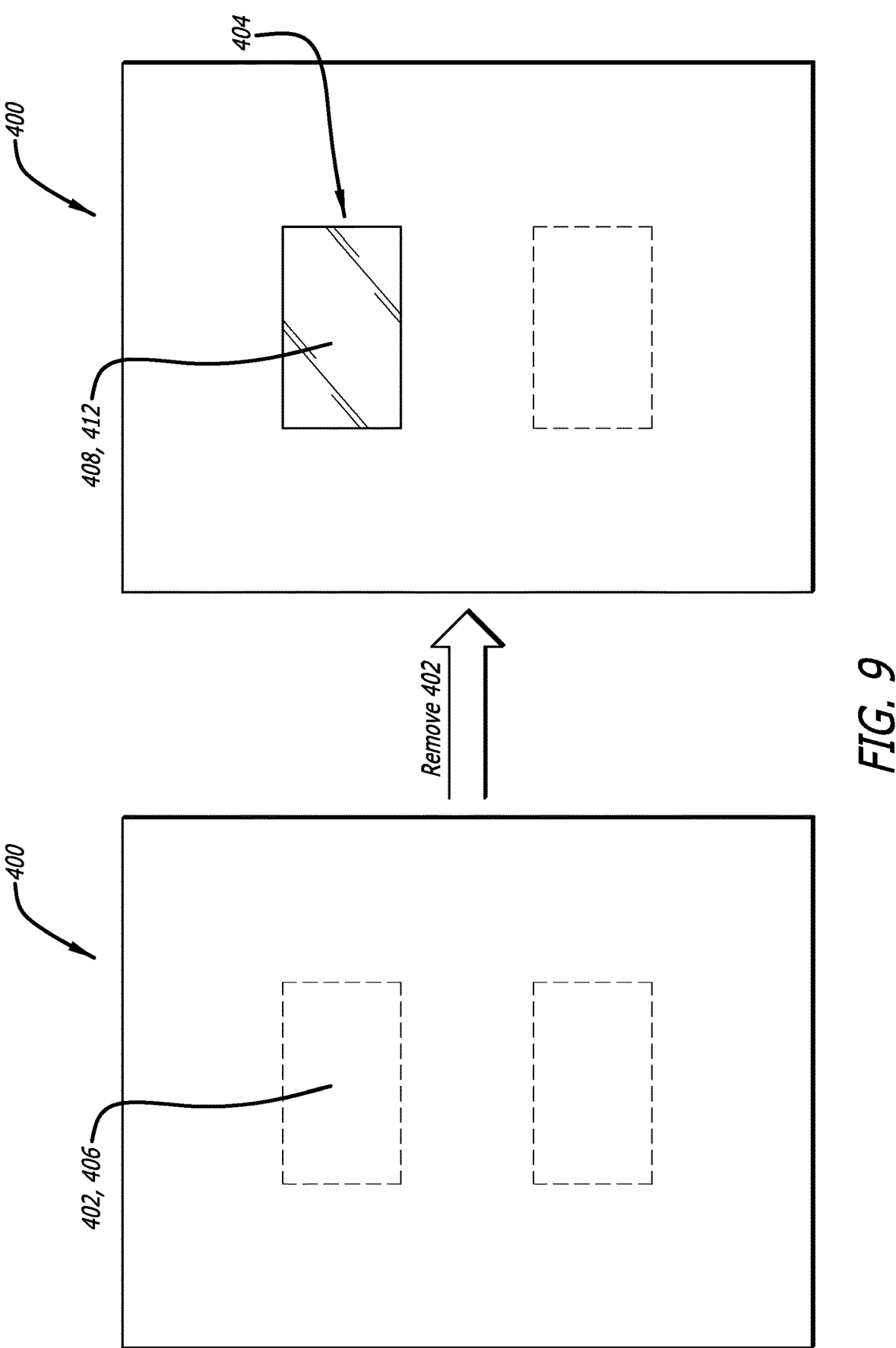
FIG. 9 illustrates removing a removable piece of the procedural drape of FIG. 6 in accordance with some embodiments.

FIG. 6 illustrates a top view of a procedural drape 400 with one or more removable pieces 402 for respectively forming one or more fenestrations 404 in accordance with some embodiments. FIGS. 7 and 8 illustrate a side view of the procedural drape 400 of FIG. 6 in accordance with some embodiments. FIG. 9 illustrates removing a removable piece of the procedural drape 400 of FIG. 6 in accordance with some embodiments.

The procedural drape 400 is configured to cover a patient or one or more portions of the patient for a medical procedure. For example, the procedural drape 400 can be a sterile drape configured to cover the patient or the one-or-more portions of the patient.

The procedural drape 400 includes an opaque sheet 406 of one or more nonwoven materials, a transparent sheet 408 of polymeric material on a side of the opaque sheet 406 forming a laminate thereof (see FIG. 7), and the one-or-more removable pieces 402 of the opaque sheet 406 configured for respectively forming the one-or-more fenestrations 404 in the opaque sheet 406 upon removal of the one-or-more removable pieces 402 from the procedural drape 400. A same or different opaque sheet 410 of the one-or-more nonwoven materials including the same one-or-more removable pieces 402 is optionally on a side of the transparent sheet 408 forming another laminate (see FIG. 8). The procedural drape 400 including at least the opaque sheet 406 and the transparent sheet 408 has a length and width sufficient to establish a procedural field about the patient with the transparent sheet 408 providing one or more fenestration coverings 412 respectively covering the one-or-more fenestrations 404 formed upon removal of the one-or-more removable pieces 402 from the procedural drape 400, thereby allowing a clinician to manipulate the patient, one or more pieces of procedural equipment or supplies, or a combination thereof under the one-or-more fenestration coverings 412 having a flexibility therefor.

The opaque sheet 406 includes a single ply of the one-or-more nonwoven materials or two or more plies of the one-or-more nonwoven materials. The nonwoven material of any ply of the opaque sheet 406 can be a polypropylene or a wood pulp. In other words, the single ply or each ply of the two-or-more plies of the opaque sheet 460 can independently be a polypropylene or a wood pulp. For example, the opaque sheet 406 can be a single ply of spunbond polypropylene. Alternatively, the opaque sheet 406 can be a single ply of spunlace wood pulp. Such embodiments are exemplified in the main portions of FIGS. 7 and 8. In another example, the opaque sheet 406 includes one ply of meltblown polypropylene between two plies of spunbond polypropylene. Such an embodiment is exemplified in the inset portion of FIG. 7.

The transparent sheet 408 includes a single non-laminated transparent sheet of polymeric material or two-or-more layers of polymeric material laminated together in a laminated transparent sheet. Regardless, the transparent sheet 408 is coextensive with the length and the width of the opaque sheet 406. Like that set forth above, the polymeric material of the transparent sheet 408 can be a porous, breathable polymeric film such as a polyethylene, a polypropylene, or a polyurethane. For the laminated transparent sheet, each layer of the two-or-more layers can include a same or different polymeric material than an adjacent layer of the two-or-more layers of the laminated transparent sheet. The polymeric material in the non-laminated transparent sheet or in any layer of the two-or-more layers of the laminated transparent sheet can also be impregnated with a broad-spectrum antimicrobial (e.g., an iodophor) to impart antimicrobial activity to the fenestration covering 412.

The procedural drape 400 also includes margins around a central portion 414 of the procedural drape 400 such as a pair of opposing longitudinal margins 416 and a pair of opposing transverse margins 418. One pair or both pairs of margins of the pairs of longitudinal and transverse margins 416 and 418 can include a single-use or reusable adhesive configured for adhering the procedural drape 400 to one or more other procedural drapes or surfaces.

The one-or-more removable pieces 402 of the opaque sheet 406 can be of any shape or size for respectively forming the one-or-more fenestrations 404 in the opaque sheet 406 of a corresponding shape or size upon removal of the one-or-more removable pieces 402 from the opaque sheet 406. The one-or-more removable pieces 402 can have perforated or precut perimeters configured to facilitate removal of the one-or-more removable pieces 402 from the opaque sheet 406. The one-or-more removable pieces 402 can include a reusable adhesive configured for adhering the one-or-more removable pieces 402 to the transparent sheet 408. The reusable adhesive can be the same adhesive as the foregoing adhesive for adhering the procedural drape 400 to one or more other procedural drapes or surfaces. Such an adhesive is particularly useful in embodiments of the procedural drape 400 in which the one-or-more removable pieces 402 have precut perimeters.

Being that the one-or-more fenestration coverings 412 respectively covering the one-or-more fenestrations 404 upon formation thereof are provided by the transparent sheet 408, the one-or-more fenestration coverings are breachable by a piece of procedural equipment of the one-or-more pieces of procedural equipment. Like that set forth above, this is useful for connecting sterile consumable equipment in a sterile field above a sterile procedural drape to non-sterile reusable equipment below the procedural drape 400.

Methods

Methods of fenestration coverings and procedural drapes include methods of using the fenestration coverings and procedural drapes. For example, a method for the fenestration covering 100 includes a forming step, a covering step, and a manipulating step.

The forming step includes forming a fenestration in one or more procedural drapes for a medical procedure. For example, the forming step can include cutting out at least one piece of at least one procedural drape of the one-or-more procedural drapes to form the fenestration. A cutting device such as a scalpel or a hoop with a serrated edge could be used to form the fenestration in the one-or-more procedural drapes. Optionally, a palpable cutting surface as part of some reusable equipment is placed below the one-or-more procedural drapes before such cutting. Alternatively, the forming step includes arranging several procedural drapes of the one-or-more procedural drapes around an area of the patient to form the fenestration among the several procedural drapes.

The covering step includes covering the fenestration with the fenestration covering 100. If sterile consumable equipment in a sterile field above a sterile procedural drape needs to be connected to non-sterile reusable equipment below the procedural drape in a connecting step, the connecting step can be performed before the covering step. Otherwise, the connecting step is performed after the covering step, which requires breaching the fenestration covering 100. As set forth above, the fenestration covering 100 includes the transparent sheet 102 of polymeric material having a length and width sufficient to cover the fenestration. The fenestration covering 100 also includes a non-adhesive central portion 104 of the fenestration covering 100 that is greater than or coextensive with the fenestration.

The manipulating step includes manipulating the patient, one or more pieces of procedural equipment or supplies, or a combination thereof under the fenestration covering 100.

The method can further include an adhering step. The adhering step includes adhering the fenestration covering 100 to the one-or-more procedural drapes. As set forth above, the fenestration covering 100 can include margins around the central portion of the fenestration covering including the pair of opposing longitudinal margins 106 and the pair of transverse margins 108 in which at least one pair or both pairs of margins of the pairs of longitudinal and transverse margins 106 and 108 can include a single-use or reusable adhesive configured for the adhering step.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A procedural drape for a medical procedure, comprising:

a first opaque sheet of one or more nonwoven materials, the first opaque sheet having a length and width sufficient to establish a procedural field about a patient for the medical procedure;

a transparent sheet of polymeric material on a side of the first opaque sheet forming a laminate with the first opaque sheet, the transparent sheet coextensive with the length and the width of the first opaque sheet;

a second opaque sheet of one or more nonwoven materials on a side of the transparent sheet, thereby further forming the laminate; and one or more removable pieces of the first opaque sheet configured for respectively forming one or more fenestrations in the first opaque sheet upon removal of the one or more removable pieces, one or more fenestrations in the second opaque sheet matching the one or more fenestrations in the first opaque sheet when formed, and one or more fenestration coverings of the transparent sheet covering the one or more fenestrations of the first opaque sheet when formed, wherein the one or more fenestration coverings are breachable by a piece of procedural equipment.

2. The procedural drape of claim 1, wherein the one or more removable pieces have perforated or precut perimeters configured to facilitate removal of the one or more removable pieces.

3. The procedural drape of claim 1, wherein the one or more removable pieces include a reusable adhesive configured for adhering the one or more removable pieces to the transparent sheet.

4. The procedural drape of claim 1, further comprising margins around a central portion of the procedural drape, the margins including a pair of opposing longitudinal margins and a pair of transverse margins in which at least one pair of margins of the pairs of opposing longitudinal and transverse margins includes a same or different reusable adhesive configured for adhering one or more procedural drape surfaces.

5. The procedural drape of claim 1, further comprising margins around a central portion of the procedural drape, the margins including a pair of opposing longitudinal margins and a pair of transverse margins in which at least one pair of margins of the pairs of opposing longitudinal and transverse margins includes a single-use adhesive configured for adhering one or more procedural drape surfaces.

6. The procedural drape of claim 1, wherein the first opaque sheet includes one or more plies, each ply of the one or more plies of the one or more nonwoven materials selected from a polypropylene or a wood pulp.

7. The procedural drape of claim 6, wherein the first opaque sheet includes a single ply of spunbond polypropylene.

8. The procedural drape of claim 6, wherein the first opaque sheet includes a single ply of spunlace wood pulp.

9. The procedural drape of claim 6, wherein the first opaque sheet includes one ply of meltblown polypropylene between two plies of spunbond polypropylene.

10. The procedural drape of claim 1, wherein the polymeric material is a breathable polyethylene, a polypropylene, or a polyurethane.

11. The procedural drape of claim 1, wherein the polymeric material is impregnated with a broad-spectrum antimicrobial.

12. The procedural drape of claim 1, wherein the procedural drape is a sterile procedural drape.

13. A procedural drape for a medical procedure, comprising:

a first opaque sheet of one or more nonwoven materials, the first opaque sheet having a length and a width adapted to establish a procedural field about a patient for the medical procedure;

a transparent sheet of polymeric material on a side of the first opaque sheet forming a laminate with the first opaque sheet, the transparent sheet coextensive with the length and the width of the first opaque sheet;

a second opaque sheet of one or more nonwoven materials on a side of the transparent sheet, thereby further forming the laminate; and one or more fenestrations in the first opaque sheet, one or more fenestrations in the second opaque sheet matching the one or more fenestrations in the first opaque sheet, and one or more fenestration coverings of the transparent sheet covering the one or more fenestrations of the first opaque sheet, wherein the one or more fenestration coverings are breachable by a piece of procedural equipment.

14. The procedural drape of claim 13, wherein the polymeric material is impregnated with a broad-spectrum antimicrobial.

15. The procedural drape of claim 14, wherein the broad-spectrum antimicrobial is an iodophor.

16. The procedural drape of claim 13, further comprising margins around a central portion of the procedural drape, the margins including a pair of opposing longitudinal margins and a pair of transverse margins in which at least one pair of margins of the pairs of opposing longitudinal and transverse margins includes a reusable adhesive configured for adhering one or more procedural drape surfaces.

17. The procedural drape of claim 13, further comprising margins around a central portion of the procedural drape, the margins including a pair of opposing longitudinal margins and a pair of transverse margins in which at least one pair of margins of the pairs of opposing longitudinal and transverse margins includes a single-use adhesive configured for adhering one or more procedural drape surfaces.

18. The procedural drape of claim 13, wherein the first opaque sheet includes one or more plies, each ply of the one or more plies of the one or more nonwoven materials selected from a polypropylene and a wood pulp.

19. The procedural drape of claim 18, wherein the first opaque sheet includes a single ply of spunbond polypropylene.

20. The procedural drape of claim 18, wherein the first opaque sheet includes a single ply of spunlace wood pulp.

21. The procedural drape of claim 18, wherein the first opaque sheet includes one ply of meltblown polypropylene between two plies of spunbond polypropylene.

22. The procedural drape of claim 13, wherein the polymeric material is a breathable polyethylene, a polypropylene, or a polyurethane.

23. The procedural drape of claim 13, wherein the procedural drape is a sterile procedural drape.

* * * * *